United States Patent [19]  [11] 4,329,868
Kuznetsov et al.  [45] May 18, 1982

[54] METHOD FOR THE DETERMINATION OF HYDROGEN CONTENT IN INORGANIC MATERIALS

[76] Inventors: Lev B. Kuznetsov, ulitsa Pljuschikha, 42, korpus 1, kv. 47, Moscow; Valentin V. Strelkov, ulitsa Gorkogo, 164, kv. 194; Anatoly V. Zaitsev, pereulok Shkolny, 50, kv. 44, both of Izhevsk; Igor A. Lvov, ulitsa B. Gruzinskaya, 36-a, kv. 9; Valentina P. Romanova, ulitsa Svobody, 3, kv. 44, both of Moscow, all of U.S.S.R.

[21] Appl. No.: 113,334

[22] Filed: Jan. 18, 1980

[51] Int. Cl.³ ............................................. G01N 7/16
[52] U.S. Cl. ..................................................... 73/19
[58] Field of Search ..................................... 73/19, 23

[56] References Cited

U.S. PATENT DOCUMENTS

| | | | |
|---|---|---|---|
| 3,177,700 | 4/1965 | Sier | 73/19 |
| 3,188,180 | 6/1965 | Höller | 73/19 |
| 3,498,105 | 3/1970 | Hetherington | 73/19 |
| 3,905,222 | 9/1975 | Boillot | 73/19 |
| 4,142,399 | 3/1979 | Sato et al. | 73/19 |

Primary Examiner—Stephen A. Kreitman
Attorney, Agent, or Firm—Steinberg & Raskin

[57] ABSTRACT

A sample of an inorganic material is placed into a hermetically sealed electrode pulse furnace and heating and melting of the sample are effected at a temperature within the range of from 1,600° to 2,500° C. Delivering of the hydrogen evolved upon melting from the unsealed furnace to the site of its quantitative recording is effected by means of an inert gas at a temperature of from 1,600° to 2,500° C., which makes it possible to determine the content of hydrogen with an accuracy of $2 \times 10^{-3}\%$ by mass in inorganic materials, for example slags, within a period of from 5 to 10 minutes.

2 Claims, No Drawings

METHOD FOR THE DETERMINATION OF HYDROGEN CONTENT IN INORGANIC MATERIALS

The present invention relates to metallurgy and, more particularly, to a method for the determination of hydrogen content in inorganic materials such as slags resulting from metallurgic processes.

FIELD OF THE INVENTION

The method according to the present invention is useful in steel-melting, blast-furnace processes for the determination of conditions of said processes. Furthermore, the method of the present invention can be used in non-ferrous metallurgy.

BACKGROUND OF THE INVENTION

Known in the art is a chemical method for the determination of hydrogen content, for example, in blast-furnace slag, which is based on determination of the amount of carbon dioxide produced upon reduction of water contained in the slags according to the following reactions:

$$2H_2O + 2C = 2CO + 2H_2$$

$$2H_2 + 2CuO = 2H_2O + 2Cu$$

$$2H_2O + CaC_2 = Ca(OH)_2 + C_2H_2$$

$$C_2H_2 + 5CuO = 2CO_2 + H_2O + 5Cu.$$

However, this is not a versatile method, since it is suitable only for blast-furnace slags, is labour-consuming and takes a long time of from 4 to 6 hours. The greatest difficulties are encountered in the determination of hydrogen content in fluorine-containing slags, wherefrom from which hydrogen can be evolved upon heating in the form of $H_2$, $H_2O$ and $HF$. In order to avoid losses, the total combined hydrogen content should be converted to free hydrogen. Very complicated transformations are used for analysis of fluorine-containing slags in a current of oxygen at the temperature of 1,200° C. which, apart from complicating the analytical procedure, cause possible errors.

Also known in the art is a method for the determination of hydrogen in oxide melts which involves melting a sample at the temperature of 1,600° C. in an inert gas current. The water liberated from the slag and carried-off by the gas current is passed to, for example, a quartz pipe filled with ferromolybdenum, wherein it is reduced to hydrogen and carbon dioxide. The amount of hydrogen is determined by one of the conventional methods such as by chromatography. This method is rather complicated and labour-consuming and takes about 1-2 hours for the determination.

Another known method for the determination of hydrogen content in metals involves melting of a metal sample in a graphite crucible placed into an electrode pulse furnace at a temperature within the range from 1,800° to 3,000° C. Melting of the metal sample is effected in a current of a carrier gas intended for delivering the evolved hydrogen to the site of its quantitative recording, for example a thermal conductivity sensor.

In the use of this method for the determination of hydrogen amount in slags (due to the fact that hydrogen in slags is in the form of water) there occurs an incomplete reduction of water to hydrogen due to a continuous removal of water vapours from the reaction zone and, consequently, lowered results are obtained in the determination of hydrogen.

It is an object of the present invention to overcome the above-mentioned disadvantages.

It is an object of the present invention to provide such a method for the determination of hydrogen content which makes it possible to determine the amount of hydrogen in inorganic materials, for example slags, with maximum possible accuracy.

It is another object of the present invention to provide such a method which makes it possible to determine the amount of hydrogen in inorganic materials, for example slags, within the shortest possible time and at minimum possible labour expenses.

BRIEF SUMMARY OF THE INVENTION

These objects are accomplished in the determination of hydrogen content in inorganic materials by the method involving melting of a sample in a furnace in a graphite crucible at a temperature within the range of from 1,600° to 2,500° C. in an inert gas atmosphere and delivery of the hydrogen evolved upon melting in a current of an inert gas to the site of its quantitative recording, wherein, in accordance with the present invention said melting of the sample is effected in a hermetically sealed furnace during the period of time sufficient for complete removal of hydrogen-compounds from the sample, whereafter the hydrogen evolved is discharged from the furnace at the above-specified temperature.

The method according to the present invention makes it possible to determine, within the period of from 5 to 10 minutes, the amount of hydrogen with an accuracy of $2 \times 10^{-3}\%$ by mass in inorganic materials, for example in slags. Furthermore, the method according to the present invention can be readily automated.

Further objects and advantages of the present invention will now become more fully apparent from the following detailed description of the method for the determination of hydrogen content in inorganic materials and Examples illustrating its embodiments.

DETAILED DESCRIPTION OF THE INVENTION

The method according to the present invention is suitable for the determination of the amount of hydrogen in slags (resulting from blast-furnace processes, steel-making) fluxes, crystalhydrates and other inorganic materials containing hydrogen in both free form and as water.

To practise the method of the present invention use is made of e.g. electrode pulse or induction furnaces of conventional arrangement having a graphite crucible.

The sample to be analyzed, for example slag, is placed into a graphite crucible preliminary outgassed at a temperature of 2,000° to 3,000° C. in a current of an inert gas. Thereafter, the crucible with the sample is repeatedly purged with an inert gas for 5 to 10 seconds.

In accordance with the present invention, prior to melting of the test sample the working space of the furnace should be hermetically sealed in order to provide conditions for a more complete proceeding of the reaction of reducing water to hydrogen. The temperature at which water contained in the sample is reduced to hydrogen is within the range of from 1,600° to 2,500° C. depending on the nature of the analyzed material; for example, in the determination of the amount of hydrogen in borax $Na_2O_2B_2O_3.10H_2O$ the process temperature is varied within the range of from 2,200° to 2,400° C.

It has been found that for a complete progress of the process 3 to 15 seconds are sufficient, (however this time may vary depending on the kind of material) i.e. within this period complete removal of the hydrogen-containing compounds from the sample occurs. Then the furnace, without discontinuing the heating thereof, is unsealed and the evolved hydrogen is delivered to an analyzer such as a chromatograph by means of an inert carrier gas, for example argon. Due to the fact that the evolved hydrogen is withdrawn from the furance without interrupting the heating thereof, i.e. at a temperature of 1,600° to 2,500° C., it has become possible to attain a more complete reduction of the water vapours that evolved from the sample being analyzed and are found in the reaction zone (on the walls of the reaction vessel and within the pores of the furnace members).

The present method makes it possible to determine the hydrogen content in the analyzed inorganic material with an accuracy to $2.10^{-3}$ mass %.

EXAMPLE

Hydrogen content is determined in a sample of borax $Na_2O_2B_2O_3.10H_2O$ on a unit with pulse heating and a chromatograph.

A sample weighing 0.02 g is placed into a charging device and a graphite crucible with a batch of tin (0.05 g) is placed into a furnace. Tin serves to preclude the absorption of hydrogen by graphite sublimates.

The graphite crucible is degassed at a temperature of 3.000° C. by passing a current pulse for 6 seconds and purging the furnace volume with purified argon to remove the gases to the atmosphere. Then the furnace heating is switched off, the borax sample by means of the charging device is transferred to the graphite crucible, the furnace is purged with argon for 10 seconds, then the furnace volume is sealed, heating thereof is switched on, and melting of a sample is effected at the temperature of 2,300° C. for 4 seconds. Then, without switching off the furnace heating, the furnace is unsealed, and the reaction product is transferred to the chromatograph through the agency of a stream of argon.

The results of the determination of the amount of hydrogen in borax obtained by the method according to the present invention and by the prior art method are shown in the following Table.

TABLE

| Method of analysis | Temperature, °C. | Number of determinations | Amount of the evolved hydrogen, % |
|---|---|---|---|
| 1 | 2 | 3 | 4 |
| Purging of the furnace working space with an inert gas during melting of the sample | 2,300 | 20 | 55 ± 18 |
| With sealing of the furnace working space during heating and melting of the sample | 2,300 | 20 | 96 ± 8 |

Therefore, the method according to the present invention makes it possible to perform determination of the content of hydrogen in inorganic materials with high accuracy and sensitivity.

The application of the method according to the present invention in, for example, the metallurgical industry will make it possible to obtain reliable data on the content of hydrogen in slags which is one of the most important preconditions of the production of a high-quality metal.

What is claimed is:

1. Method of determining the hydrogen content in inorganic materials, which comprises melting a sample in a hermetically sealed electrode pulse furnace in a graphite crucible at a temperature within the range of from 1,600° to 2,500° C. in an inert atmosphere for a time sufficient for complete removal of hydrogen-containing compounds from the sample; and, while maintaining said temperature of from 1,600° to 2,500° C. in said furnace, unsealing said furnace and delivering the hydrogen evolved upon melting to the site of its quantitative recording by means of an inert gas at said temperature of from 1,600° to 2,500° C., whereby substantially complete reduction of the hydrogen-containing compounds from said sample is obtained and the hydrogen content of said sample is determined with a high degree of accuracy.

2. Method according to claim 1 wherein said melting of said sample is effected during a time period of 3-15 seconds.

* * * * *